United States Patent [19]
Möller et al.

[11] Patent Number: 6,103,502
[45] Date of Patent: *Aug. 15, 2000

[54] ULTRAFILTRATION PROCESS FOR DESALINATION AND CONCENTRATION OF A PEPTIDE IN A CELL-FREE FERMENTATION MEDIUM

[75] Inventors: Jörg Möller, Bad Soden; Frank Richard, Kronberg, both of Germany

[73] Assignee: Aventis Pharma Deutschland GmbH, Frankfurt am Main, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/755,114

[22] Filed: Nov. 22, 1996

[30] Foreign Application Priority Data

Nov. 24, 1995 [DE] Germany ............................ 195 43 737

[51] Int. Cl.⁷ ............................ C12P 21/04; C12P 21/06; C12P 1/00; C07K 1/34
[52] U.S. Cl. ........................ 435/71.1; 435/41; 435/69.1; 435/69.2; 435/814; 530/414
[58] Field of Search .......................... 435/41, 68.1, 69.1, 435/69.2, 71.1, 814; 530/350, 412, 414

[56] References Cited

U.S. PATENT DOCUMENTS

| | | | |
|---|---|---|---|
| 5,180,668 | 1/1993 | Crause et al. | 435/69.2 |
| 5,422,249 | 6/1995 | Liersch et al. | 435/69.2 |
| 5,468,844 | 11/1995 | Smith | 530/366 |
| 5,616,476 | 4/1997 | Crause et al. | 435/69.1 |

FOREIGN PATENT DOCUMENTS

| | | |
|---|---|---|
| 0158564 | 10/1985 | European Pat. Off. . |
| 0158986 | 10/1985 | European Pat. Off. . |
| 0168342 | 1/1986 | European Pat. Off. . |
| 0171024 | 2/1986 | European Pat. Off. . |
| 0193175 | 9/1986 | European Pat. Off. . |
| 0209061 | 1/1987 | European Pat. Off. . |
| 0311283 | 4/1989 | European Pat. Off. . |
| 0324712 | 7/1989 | European Pat. Off. . |
| 0610729 | 8/1994 | European Pat. Off. . |
| 0200655 | 11/1996 | European Pat. Off. . |
| 3342199 | 5/1984 | Germany . |
| 255943 | 4/1988 | Germany . |
| 3445517 | 11/1993 | Germany . |
| 8603517 | 6/1986 | WIPO . |

OTHER PUBLICATIONS

Scott K., Handbook of Industrial Membranes, 1995 Elsevier Science Publishers LTD., pp. 32–33.

Brockelbank, et al., "Primary Separation" Chap. 4in G. Schmidt–Kastner et al., Hsg.: "Recovery of Bioproducts", European Federation of Biotechnology, Study Report of Working Party on Downstream Processing, 1993, pp. 1–130.

Eriksson, Desalination, 53:259–263 (1985), "Some Examples Of The Use of Crossflow Filtration In The Downstream Processing In A Biochemical Industry".

Winzeler, Chimia, 44:288–291 (1990), "Membran–Filtration mit hoher Trennleistung und minimalem Energiebedarf" (In German).

Müller et al., Chem. Ing.–Tech. 62:(5):380–390 (1990), "Die Chromatographie, eine zentrale Methode in der biotechnischen Aufarbeitung" (In German).

Sullivan et al., Chem. Eng. Prog. 80(1):68–75 (1984), Use of this membrane separation technique will accelerate because of its economic and processing advantages and the availability of new membrane materials.

Flaschel et al., Adv. In Biochem. Engineering/Biotechnology, vol. 26, Downstream Processing, S. 73–142, N.Y. (1983); Ed.: D.J. Bell.

Atkinson et al., Biochem. Engineering and Biotechnology Handbook, Chap. 16, "Downstream Processing" and Chap. 17m "Product Recovery Processes and Unit Operations", Second Ed., Stockton Press 1991, New York.

Dodt et al., Biol. Chem. Hoppe–Seyler, 366:379–385 (1985), "The Complete Covalent Structure of Hirudin".

Markwardt, Biomed. Biochem. Acta, 44:1007–1013 (1985), "Pharmacology of Hirudin: One hundred years after the first report of the anticoagulant agent in medicinal leeches".

*Primary Examiner*—David M. Naff
*Attorney, Agent, or Firm*—Foley & Lardner

[57] ABSTRACT

A peptide such as in a cell-free fermentation medium is ultrafiltered with a membrane having a molecular weight cut-off of at least approximately two times greater than the molecular weight of the peptide. The peptide is retained by the membrane, and is desalinated and concentrated to provide prepurification of the peptide. A preferred temperature for ultrafiltration is about 5 to about 15° C. Permeate flow rate may be about 10 l/m²/h to about 35 l/m²/h, and permeate conductivity may be less than about 10 mS/cm. The permeate may be recycled until peptide concentration is constant. A cell-free fermentation medium containing hirudin from a recombinant microorganism such as *Saccharomyces cerevisiae* is ultrafiltered with a membrane having a molecular weight cut-off of about 20 kD to about 30 kD.

20 Claims, No Drawings

ULTRAFILTRATION PROCESS FOR DESALINATION AND CONCENTRATION OF A PEPTIDE IN A CELL-FREE FERMENTATION MEDIUM

BACKGROUND OF THE INVENTION

1. Field of the Invention

The present invention relates to an utrafiltration process for prepurification of complex biological matrices, in particular fermentation medium, which comprise a desired peptide or protein.

2. Description of the Related Art

To isolate and purify a protein or peptide from fermentation medium, for example, by means of chromatographic methods, a prepurification must first be carried out. In many cases, this comprises desalination of the fermentation medium.

The need to isolate a protein or peptide from fermentation medium typically arises in the context of recombinant microorganisms transformed with suitable expression vectors. Desired proteins or peptides, for the present ultrafiltration process, are typically a recombinantly produced protein or peptide. Often, the desired protein or peptide may contain an overall charge due to a greater overall concentration of basic or acid amino acid residues. A preferred protein or peptide contain an overall positive or negative charge of 2 or larger. Also preferred is a protein or peptide with an overall charge of 4 or larger.

The utility of this process may be demonstrated by the isolation of the thrombin inhibitor hirudin, a single-chain protein with 65 amino acids, from the culture supernatant of the yeast strain *Saccharomyces cerevisiae* modified by genetic engineering.

The polypeptide hirudin, originally isolated from the leech Hirudo medicinalis, is a highly specific thrombin inhibitor with a broad therapeutic potential (F. Markward, Biomed. Biochim. Acta 44 (1985) 1007–1013). Hirudin is characterized by a high proportion of dicarboxylic acids. Isolation from native sources is not commercially practical in light of the amounts required for medical utility; such an amount can be prepared only by a genetic engineering route via transformed microorganisms. It has been found in this context that the yeast *Saccharomyces cerevisiae* is a suitable host organism for producing correctly folded and fully active hirudin (EP A1 168 342, EP A1 200 655). Secretion of the protein results in concentrations of up to a few hundred milligrams of hirudin per liter of culture filtrate. A higher yield of the protein may be achieved if nutrient medium, or fermentation medium, is further enriched with additional nutrients, such as, yeast extract, corn steep, peptone or meat paste. Such additional nutrients are often protein-like substances, or contain additional protein from which the desired protein must be separated during the purification process. Therefore, use of enriched fermentation medium, while increasing protein yield, complicates ultimate purification of the protein, as there is the additional problem of isolating hirudin from a high dilution in a mixture of protein-like concomitant substances.

Methods of desalination of fermentation mediums as prepurification in preparation for chromatograph stages have included conventional methods, such as, extraction or precipitation, and hydrophobic adsorptions/desorptions, for example, on non-polar polymer materials (also HIC), (Atkinson, F. Mavituna; Biochemical Engineering and Biotechnology Handbook, Chapter 16 "Downstream Processing" and Chapter 17 "Product Recovery Processes and Unit Operations", Second Edition, Stockton Press 1991, New York, U.S.A; Brocklebank, M. Kalyanpur: "Primary Separation", Chapter 4 in G. Schmidt-Kastner et al., editors: "Recovery of Bioproduct", European Federation of Biotechnology, Study Report of Working Party on Downstream Processing, 1993; Müller and W. Brümmer: "Die Chromatographie, eine zentrale Methode in der biotechnischen Aufarbeitung" [Chromatography, a central method in biotechnical workup], Chem. Ing.-Tech. 62 (1990) No. 5, pages 380–390). These processes usually involve large amounts of solvents or salts, compared with the amount of product to be prepared, which may result in additional costs or increased technical complexity for recovery and/or disposal of the solvents or salts. Furthermore, the spent adsorption resins are additional waste products.

In contrast, an object of the present invention is to provide, as prepurification process of peptide-containing fermentation medium, a membrane ultrafiltration process for the fermentation medium to a degree required for the subsequent purification steps, with high retention of the peptide or protein. The present process is particularly useful for desalination and concentration of the desired peptide.

Ultrafiltration processes for the prepurification of fermentation medium in preparation for chromatography stages have not been employed to date on a large industrial scale on these early process stages—apart from for the purpose of removal of cells (T .J. O'Sullivan et al. Chem. Eng. Prog. 80 (1), 68–75 (1984); A. Erikson, Desalination, 53 (1985), 259–263). One reason for this is that the membranes are often blocked by the by-products and concomitant substances, which may be diverse in nature, and therefore lead to slow permeate flow rates, which for production purposes are unsuitably low. Additional problems also result in the cleaning or regeneration of the membranes (Winzeler: "Membran-Filtration mit hoher Trennleistung und minimalem Energiebedarf" [Membrane filtration with a high separation efficiency and minimal energy requirement], Chimia 44 (1990) 288–291). The present process particularly applies to preparation of a protein of low molecular weight (M<50,000 Dalton) and peptides, which supposedly require ultrafiltration membranes with very low molecular weight cut-off.

Processes are known where only at later process stages, after prepurification has already taken place, for example between successive chromatography stages, are ultrafiltrations performed, for example for desalination and concentration.

Membrane ultrafiltration processes are also used for separation of protein of different size, for removal of pyrogens or for isolation of biocatalysts (T. J. O'Sullivan et al., Chem. Eng. Prog. 80(1), 68–75 (1984); E. Flaschel et al., Adv. in Biochem. Engineering/Biotechnologie Volume 26, "Downstream Processing", pages 73–142, N.Y. 1983; Editor: D. J. Bell). EP 610 729 A1 discloses a process for the purification of protein or peptide by ultrafiltration, in which the nominal molecular weight cut-off of the ultrafiltration membrane is greater than the molecular weight of the protein to be purified, where the protein passes through the membrane.

Insulin undergoes reversible agglomeration, where higher aggregates, particularly insulin hexamers, under special conditions, dissociate. DD 225 943 A1 discloses an ultrafiltration process for the purification of insulin aggregates under special conditions favoring aggregation of insulin molecules. DD 225 943 A1 reference discloses a membrane with a molecular cut-off nearly equal to or smaller than the molecular weight of insulin aggromerates and insulin hexamers, but still larger than the molecular weight of single insulin molecule.

The processes mentioned are all based on the principle of employing, for filtration of a peptide or a protein, a membrane of molecular weight cut-off in or below the molecular weight range of the peptide or protein to be retained.

SUMMARY OF THE INVENTION

It has now been found that it is entirely possible to desalinate and concentrate a protein or peptide having a low molecular weight with very high retention of the product on membranes which have a nominal molecular weight cut-off of up to about 30,000 Daltons.

As used herein, the term "peptide" is intended to include both protein and peptide. Generally, a peptide is a small fragment of protein. In addition, the singular term also includes the separation of different proteins or peptides.

As used herein, terms such as "conductivity", "permeate" and "filtrate" are terms of the art readily understood by those skilled in the art and are intended to mean as commonly defined in texts such as Atkinson, F. Mavituna; Biochemical Engineering and Biotechnology Handbook, Second Edition, Stockton Press 1991, New York, U.S.A; Brocklebank, M. Kalyanpur: "Primary Separation", Chapter 4 in G. Schmidt-Kastner et al., editors: "Recovery of Bioproduct", European Federation of Biotechnology, Study Report of Working Party on Downstream Processing, 1993; Müller and W. Brümmer: "Die Chromatographie, eine zentrale Methode in der biotechnischen Aufarbeitung" [Chromatography, a central method in biotechnical workup], Chem. Ing.-Tech. 62 (1990) No. 5, pages 380–390), incorporated by reference herein.

The present invention accordingly also relates to a process for prepurification of a cell-free culture medium comprising a peptide by means of ultrafiltration on a membrane, wherein the stated molecular weight cut-off of the membrane is approximately two to approximately five times, preferably approximately three to approximately four times, the molecular weight of the peptide or protein to be retained by the membrane. Ultrafiltration membranes are characterized, in addition to other properties, by their nominal molecular weight cut-off. All the molecules larger than the molecular weight cut-off of a particular membrane are generally retained and those smaller than the molecular weight cut-off level generally pass through the membrane. Atkinson and Mativuna; Biochemical Engineering and Biotechnology Handbook, Chapter 17, "Product Recovery Processes and Unit Operations", 2nd Ed., Stockton Press 1991, NY, USA see page 978.

DETAILED DESCRIPTION OF THE INVENTION

The present invention is used in particular for prepurification of cell-free culture medium which comprise a recombinant hirudin, in particular a hirudin which is expressed in *Saccharomyces cerevisiae*.

The present invention also relates to products made according to the disclosed process and compositions comprising such products. As used herein, "hirudin" is to be understood as meaning peptide-like thrombin inhibitors having a specific activity of at least 1000 AT-U/mg, which are derived from the known isohirudins of the species Hirudo medicinalis and have the essential structural features of these, in particular the characteristic linkage of the three disulfide bridges (J. Dodt et al., Biol. Chem. Hoppe-Seyler 366 (1985) 379–385); (cf. for example EP A1 158 564, EP A1 168 342, DE 34 45 517, EP A2 193 175, EP A1 200 655, EP A1 158 986, EP A1 209 061, DE 33 42 199, EP A1 171 024). The approximate molecular weight of hirudin is 7000 daltons.

In particular, this is understood as meaning of hirudin includes hirudin analogs, and especially recombinant hirudin, such as is described in EP A1 171 024, EP A1 158 986 and EP A1 209 061.

The process according to the invention is particularly preferably employed for prepurification of a cell-free fermentation medium which comprises a hirudin analog having the amino acid sequence disclosed in EP 0 324 712 and in corresponding U.S. Pat. No. 5,180,668, incorporated by reference herein, specifically, [Leu$^1$, Thr$^2$]-63-desulfohirudin. Example 1 in EP 0 324 712 and U.S. Pat. No. 5,180,668 discloses construction of a yeast expression vector, after amplification of the vector in *E. coli*, the vector is then used to transform a yeast strain, Y79.

The preferred molecular weight cut-off of the membrane for ultrafiltration of hirudin-containing culture medium is about 13 kD to about 36 kD, more preferred is about 18 kD to about 22 kD, and even more preferred is about 20 kD to about 30 kD, preferably about 20 kD.

As used herein, "permeate flow rate" is the rate at which the permeate flows through the filter. The permeate flow rate typically fluctuates during ultrafiltration. At the beginning of the ultrafiltration, the permeate flow rate is often higher than at the end of ultrafiltration because the contaminants clog the openings of the pores.

The specific permeate flow rates in the process according to the present invention are preferably an average rate of about 10 l/m$^2$/h to about 35 l/m$^2$/h over the entire course of the filtration.

The temperature of the filtrate may affect the filtration. Generally, solubility of the peptide and other cellular components increases with temperature. Therefore, ultrafiltration at too low a temperature may increase precipitation of unwanted by-products or even the desired protein. The preferred temperature is the highest temperature possible to obtain fast and effective ultrafiltration. The preferred temperature range is sufficiently to maintain the solubility of the desired protein or peptide but also avoid precipitation of unwanted by-products.

Certain nutrient media, especially those with an enriched with additives, such as corn steep, may also precipitate at higher temperatures. Corn steep-enriched media has been found to precipitate unwanted by-products at temperatures above 15° C. Therefore if corn steep is used in the fermentation medium, the temperature of the culture broth is preferably 5 to 15° C.

In the process according to the invention, the permeate is preferably recycled to the crude solution until steady-state conditions have been established, manifested by the fact that the desired peptide concentration in the permeate no longer rises, i.e. is constant.

EXAMPLE

A strain of *Saccharomyces cerevisiae*, modified by genetic engineering, according to Examples 1 to 3 of U.S. Pat. No. 5,180,668, is transformed by a vector encoding the hirudin derivative, [Leu$^1$, Thr$^2$]-63-desulfohirudin. At the end of the fermentation, the fermentation medium, a complex medium comprising corn steep and yeast extract for preparation of hirudin, 0.225±0.025% of benzalkonium chloride, for example, 0.45±0.05% of Dodigen® 226 (a 50% strength solution of a mixture of alkyldimethyl-benzyl-ammonium chlorides in water), is added to the culture to inactivate the cells and the medium is incubated for 30 minutes.

The medium is then passed via a separator or decanter to remove the cells, and is then clarified by a 2-stage layer filtration in a filter press comprising a fine and a sterilizing stage. The filtrate is cooled to temperatures of T≦15° C. to avoid renewed temperature-related precipitations, which are reversible.

The filtrate thus prepared has a conductivity of κ=6±0.5 mS/cm. The ultrafiltration unit, fitted with membranes of cellulose acetate having an exclusion limit of 20,000 Dalton (for example Nadir® UF-CA-20 in the form of 3.8 inch spiral coil modules), is first set in operation under the following conditions for 60 minutes, with recycling of the permeate:

| average transmembrane pressure | 4 ± 1 bar |
|---|---|
| volume flow per pressure tube | 4–5 m³/h |

The filtrate is then concentrated to a degree of 6:1 under the same conditions, with removal of permeate, and is subsequently subjected to diafiltration, i.e. desalinated, by addition of demineralized and filtered water (purified water), while keeping the volume constant, until the conductivity κ is ≦2.0 mS/cm. After the diafiltration, the product can be concentrated again, in order to arrive at a concentration of 8:1 in total; a conductivity of κ<2.2 mS/cm should be maintained here.

| Process data and results: | |
|---|---|
| Initial volume | 4600 l |
| Initial concentration of hirudin | 100 % |
| Final volume | 710 l |
| Final concentration of hirudin | 607.2 % |
| Initial conductivity | 5.83 mS/cm |
| Final conductivity | 1.97 mS/cm |
| Yield of hirudin | 93.7 % |
| Recovery | 96.9 % |
| Product loss in the permeate | 3.3 % |

We claim:

1. A process for the desalination and concentration of a desired peptide comprising desalinating and concentrating said peptide in a cell-free fermentation medium by ultrafiltrating said peptide on a membrane wherein the molecular weight cut-off limit of said membrane is at least approximately two times greater than the molecular weight of said peptide, and wherein said peptide is retained by membrane.

2. The process of claim 1, wherein the molecular weight cut-off limit of said membrane is approximately two to approximately five times greater than the molecular weight of said peptide.

3. The process of claim 2, wherein the molecular weight cut-off limit of said membrane is approximately two to approximately four times greater than the molecular weight of said peptide.

4. The process of claim 1, where the peptide contains an overall charge.

5. The process of claim 4, wherein the overall charge is a positive or negative charge of 2 or larger.

6. The process of claim 5, wherein the overall positive or negative charge is 4 or larger.

7. The process of claim 1, where the peptide is hirudin or an analog thereof.

8. The process of claim 7, wherein the hirudin or analog thereof is recombinantly produced.

9. The process of claim 8, wherein the hirudin or analog thereof is produced in a recombinant microorganism.

10. The process of claim 9, wherein the microorganism is a yeast.

11. The process of claim 10, wherein the yeast is *Saccharomyces cerevisiae*.

12. The process as claimed in claim 7, wherein the molecular weight cut-off of the membrane is between about 20 to about 30 kD.

13. The process of claim 1, wherein the ultrafiltration has a permeate flow rate over the entire course of the filtration of about 10 l/M²/h to about 35 l/m²/h.

14. The process of claim 1, wherein the ultrafiltration occurs at a temperature of about 5 to about 15° C.

15. The process of claim 1, wherein permeate is recycled until the peptide concentration in the permeate has assumed a constant value.

16. The process of claim 15, wherein the permeate has a conductivity of less than about 10 mS/cm.

17. The process of claim 16, wherein the permeate has a conductivity of about less than about 7 mS/cm.

18. The process of claim 17, wherein the permeate has a conductivity of less than about 3 mS/cm.

19. A desalinated and concentrated peptide obtained according to the process of claim 1.

20. A desalinated and concentrated peptide obtained according to the process of claim 7.

* * * * *